(12) United States Patent
Shea et al.

(10) Patent No.: US 11,879,034 B2
(45) Date of Patent: Jan. 23, 2024

(54) FUNCTIONALIZATION OF POLYMER SCAFFOLDS

(71) Applicant: THE REGENTS OF THE UNIVERSITY OF MICHIGAN, Ann Arbor, MI (US)

(72) Inventors: Lonnie D. Shea, Ann Arbor, MI (US); Michael Skoumal, Ann Arbor, MI (US); Ryan M. Pearson, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/491,063

(22) PCT Filed: Mar. 8, 2018

(86) PCT No.: PCT/US2018/021554
§ 371 (c)(1),
(2) Date: Sep. 4, 2019

(87) PCT Pub. No.: WO2018/165432
PCT Pub. Date: Sep. 13, 2018

(65) Prior Publication Data
US 2020/0010611 A1 Jan. 9, 2020

Related U.S. Application Data

(60) Provisional application No. 62/468,833, filed on Mar. 8, 2017.

(51) Int. Cl.
*A61K 47/50* (2017.01)
*A61K 47/64* (2017.01)
(Continued)

(52) U.S. Cl.
CPC .......... *C08G 63/912* (2013.01); *A61K 38/177* (2013.01); *A61K 47/545* (2017.08);
(Continued)

(58) Field of Classification Search
None
See application file for complete search history.

(56) References Cited

U.S. PATENT DOCUMENTS

2012/0231519 A1 9/2012 Bushman et al.
2017/0184583 A1* 6/2017 Beaumont ........ G01N 33/54366

FOREIGN PATENT DOCUMENTS

WO WO-03000234 A1 * 1/2003 .......... A61K 9/0024
WO WO-2014/014613 A2 1/2014

OTHER PUBLICATIONS

Sanal et al. (Polym. Bull. 2017;74:977-995; published online Jul. 23, 2016). (Year: 2016).*

(Continued)

*Primary Examiner* — Ernst V Arnold
(74) *Attorney, Agent, or Firm* — MARSHALL, GERSTEIN & BORUN LLP

(57) ABSTRACT

The disclosure provides a method of preparing a polymer scaffold including admixing a biotinylated reagent and a polymer to form a biotinylated polymer, subjecting the biotinylated polymer to conditions sufficient to form the polymer scaffold and optionally admixing the polymer scaffold with a streptavidin-modified biomolecule to form a biomolecule-modified polymer scaffold. The disclosure further provides a method of preparing a polymer scaffold including admixing a first click chemistry reagent and a poly(lactic-co-glycolic acid) (PLGA) polymer to form a modified PLGA polymer, subjecting the modified PLGA polymer to conditions sufficient to form the polymer scaffold, and optionally admixing the polymer scaffold with a (Continued)

biomolecule modified to include a second click chemistry reagent that selectively reacts with the first click chemistry reagent, to form a biomolecule-modified polymer scaffold.

22 Claims, 5 Drawing Sheets

(51) Int. Cl.
    C08G 63/91    (2006.01)
    A61K 47/59    (2017.01)
    A61K 47/54    (2017.01)
    A61K 47/69    (2017.01)
    A61K 38/17    (2006.01)
(52) U.S. Cl.
    CPC ............ *A61K 47/593* (2017.08); *A61K 47/64* (2017.08); *A61K 47/6927* (2017.08)

(56) References Cited

OTHER PUBLICATIONS

Guan et al. (Bioconjugate Chem. 2014;25:1282-1289) (Year: 2014).*
4-arm-PEG-Acrylate [online] retrieved on Jun. 28, 2022 from: https://laysanbio.com/clientuploads/MSDS/4%20Arm-PEG-Acrylate-10K.pdf; 2015: 2 pages. (Year: 2015).*
Solids Handling [online] retrieved on Jun. 28, 2022 from: https://www.chemengonline.com/powder-bulk-solids-handling-particle-size-distribution-analysis/; 2017: 1 page (Year: 2017).*
Cannizzaro et al. (Biotechnol Bioeng 1998;58:529-535). (Year: 1998).*
Gentile et al. (Int. J. Mol. Sci. 2014;15:3640-3659) (Year: 2014).*
Abir et al., Ovarian minimal residual disease in chronic myeloid leukaemia, Reprod. Biomed. Online, 28(2):255-60 (Feb. 2014).
Attali et al. Control of beta-cell differentiation by the pancreatic mesenchyme. Diabetes. 2007:56:1248-58.
Avilés et al., Hydrogels to modulate lentivirus delivery in vivo from microporous tissue engineering scaffolds. Drug Delivery and Translational Research. 2011;1:91-101.
Azarin et al., In vivo capture and label-free detection of early metastatic cells. Nat Commun, 2015. 6: p. 8094.
Baertschiger et al. Mesenchymal stem cells derived from human exocrine pancreas express transcription factors implicated in beta-cell development. Pancreas. 2008;37:75-84.
Barton et al. Improvement in outcomes of clinical islet transplantation: 1999-2010. Diabetes Care. 2012:35:1436-45.
Bianchi et al. Effects of islet transplantation and mesenchymal stem cell co-transplantation in the protection of diabetic neuropathy in streptozotocin-induced diabetic rats. Journal of the Peripheral Nervous System. 2014;19:S3-S.
Blomeier et al. Polymer scaffolds as synthetic microenvironments for extrahepatic islet transplantation. Transplantation. 2006;82:452-9.
Boehler et al. Lentivirus delivery of IL-10 to promote and sustain macrophage polarization towards an anti-inflammatory phenotype. Biotechnology and Bioengineering. 2014;111:1210-21.
Boehler et al., A PLG/HAp composite scaffold for lentivirus delivery. Biomaterials. 2013;34:5431-8.
Boehler et al., Tissue engineering tools for modulation of the immune response. BioTechniques. 2011;51:239-40, 42, 44 passim.
Borowiak et al. Small molecules efficiently direct endodermal differentiation of mouse and human embryonic stem cells. Cell Stem Cell. 2009;4:348-58.
Bruin et al. Maturation and function of human embryonic stem cell-derived pancreatic progenitors in macroencapsulation devices following transplant into mice. Diabetologia. 2013.
Chen et al. A small molecule that directs differentiation of human ESCs into the pancreatic lineage. Nat Chem Biol. 2009;5:258-65.
Chen et al. De Novo Formation of Insulin-Producing "Neo-beta Cell Islets" from Intestinal Crypts. Cell Reports. 2014;6:1046-58.
Citro et al., Anti-inflammatory strategies to enhance islet engraftment and survival. Current diabetes reports. 2013;13:733-44.
Demeestere et al., Orthotopic and heterotopic ovarian tissue transplantation, Hum. Reprod. Update, 15(6):649-65 (Nov.-Dec. 2009).
Demeestere et al., Ovarian function and spontaneous pregnancy after combined heterotopic and orthotopic cryopreserved ovarian tissue transplantation in a patient previously treated with bone marrow transplantation: case report, Hum. Reprod., 21(8):2010-4 (Aug. 2006).
Dolmans et al., Risk of transferring malignant cells with transplanted frozen-thawed ovarian tissue, Fertil. Steril., 99(6):1514-22 (May 2013).
Donnez et al., Frozen-thawed ovarian tissue retransplants, Semin. Reprod. Med., 27(6):472-8 (Nov. 2009).
Donnez et al., Ovarian cortex transplantation: 60 reported live births brings the success and worldwide expansion of the technique towards routine clinical practice, J. Assist. Reprod. Genet., 32(8):1167-70 (Aug. 2015).
Donnez et al., Restoration of ovarian activity and pregnancy after transplantation of cryopreserved ovarian tissue: a review of 60 cases of reimplantation, Fertil. Steril., 99(6):1503-13 (May 2013).
Duncan et al. Dynamic Transcription Factor Activity Profiles Reveal Key Regulatory Interactions During Megakaryocytic and Erythroid Differentiation. Biotechnology and Bioengineering. 2014;111:2082-94.
Duvillie et al., The mesenchyme controls the timing of pancreatic beta-cell differentiation. Diabetes. 2006;55:582-9.
Filatov et al., In Vitro Mouse Ovarian Follicle Growth and Maturation in Alginate Hydrogel: Current State of the Art, Acta Naturae, 7(2):48-56 (Apr.-Jun. 2015).
Gabitass et al., Elevated myeloid-derived suppressor cells in pancreatic, esophageal and gastric cancer are an independent prognostic factor and are associated with significant elevation of the Th2 cytokine interleukin-13. Cancer Immunology, Immunotherapy, 2011. 60(10): p. 1419-1430.
Gabrilovich et al., Myeloid-derived suppressor cells as regulators of the immune system. Nature Reviews Immunology, 2009. 9(3): p. 162-174.
Gangemi et al. Islet transplantation for brittle type 1 diabetes: the UIC protocol. Am J Transplant. 2008;8:1250-61.
Gao et al., Foxa2 controls vesicle docking and insulin secretion in mature beta cells. Cell Metabolism. 2007;6:267-79.
Gibly et al. Extrahepatic islet transplantation with microporous polymer scaffolds in syngeneic mouse and allogeneic porcine models. Biomaterials. 2011;32:9677-84.
Gibly et al., Porous scaffolds support extrahepatic human islet transplantation, engraftment, and function in mice. Cell Transplant. 2013;22:811-9.
Gower et al., Biomaterial Scaffolds for Controlled, Localized Gene Delivery of Regenerative Factors. Adv Wound Care (New Rochelle). 2013;2:100-6.
Gower et al., Modulation of leukocyte infiltration and phenotype in microporous tissue engineering scaffolds via vector induced IL-10 expression. Biomaterials. 2014;35:2024-31.
Gradwohl et al., Neurogenin3 is required for the development of the four endocrine cell lineages of the pancreas. Proceedings of the National Academy of Sciences of the United States of America. 2000;97:1607-11.
Graham et al. PLG scaffold delivered antigen-specific regulatory T cells induce systemic tolerance in autoimmune diabetes. Tissue engineering Part A. 2013;19:1465-75.
Haeno et al., Computational modeling of pancreatic cancer reveals kinetics of metastasis suggesting optimum treatment strategies. Cell, 2012. 148(1-2): p. 362-75.
Hlavaty et al. Enhancing Human Islet Transplantation by Localized Release of Trophic Factors From PLG Scaffolds. American Journal of Transplantation. 2014;14:1523-32.
Hornick et al., Isolated primate primordial follicles require a rigid physical environment to survive and grow in vitro, Hum. Reprod., 27(6):1801-10 (Jun. 2012).
Hornick et al., Multiple follicle culture supports primary follicle growth through paracrine-acting signals, Reproduction, 14591):19-32 (Jan. 2013).

(56) References Cited

OTHER PUBLICATIONS

Imthurn et al., Gonadotrophin administration can benefit ovarian tissue grafted to the body wall: implications for human ovarian grafting, Mol. Cell Endocrinol., 163(1-2):141-6 (May 2000).
International Application No. PCT/US2018/021554, International Search Report and Written Opinion, dated Jun. 18, 2018.
Jang et al., Gene delivery from polymer scaffolds for tissue engineering. Expert Review of Medical Devices. 2004;1:127-38.
Jhala et al. cAMP promotes pancreatic beta-cell survival via CREB-mediated induction of IRS2. Genes & development. 2003;17:1575-80.
Kelly et al. Cell-surface markers for the isolation of pancreatic cell types derived from human embryonic stem cells. Nat Biotechnol. 2011;29:750-6.
Kheradmand et al. Permanent protection of PLG scaffold transplanted allogeneic islet grafts in diabetic mice treated with ECDI-fixed donor splenocyte infusions. Biomaterials. 2011;32:4517-24.
Kim et al., Toward precision medicine for preserving fertility in cancer patients: existing and emerging fertility preservation options for women, J. Gynecol. Oncol., 27(2):e22 (Mar. 2016).
Klein, Parallel progression of primary tumours and metastases, Nat. Rev. Cancer, 9(4):302-12 (Apr. 2009).
Kniazeva et al., Primordial Follicle Transplantation within Designer Biomaterial Grafts Produce Live Births in a Mouse Infertility Model, Sci. Rep., 5:17709 (Dec. 2015).
Kondapalli et al., Ovarian Tissue Cryopreservation and Transplantation. Oncofertility Med. Pract. Clin. Issues Implement.:63-75 (2012).
Krizik et al. PDX-1 and Msx-2 expression in the regenerating and developing pancreas. Journal of Endocrinology. 1999;163:523-30.
Kroon et al. Pancreatic endoderm derived from human embryonic stem cells generates glucose-responsive insulin-secreting cells in vivo. Nat Biotechnol. 2008;26:443-52.
Lammert et al. Role of VEGF-A in vascularization of pancreatic islets. Curr Biol. 2003;13:1070-4.
Lammert et al., Induction of pancreatic differentiation by signals from blood vessels. Science. 2001;294:564-7.
Lammert et al., Role of endothelial cells in early pancreas and liver development. Mech Dev. 2003;120:59-64.
Landsman et al. Pancreatic Mesenchyme Regulates Epithelial Organogenesis throughout Development. Plos Biology, 9(9):e1001143 (Sep. 2011).
Laronda et al., Alginate encapsulation supports the growth and differentiation of human primordial follicles within ovarian cortical tissue, J. Assist. Reprod. Genet., 31(8):1013-28 (Aug. 2014).
Lee et al., Foxa2 controls Pdx1 gene expression in pancreatic beta-cells in vivo. Diabetes. 2002;51:2546-51.
Lee et al., Risk of malignancy in resected cystic tumors of the pancreas < or =3 cm in size: is it safe to observe asymptomatic patients? A multi-institutional report, J. Gastrointest. Surg., 12(2):234-42 (Feb. 2008).
Lerer-Serfaty et al., Attempted application of bioengineered/biosynthetic supporting matrices with phosphatidylinositol-trisphosphate-enhancing substances to organ culture of human primordial follicles, J. Assist. Reprod. Genet., 30(10):1279-88 (Oct. 2013).
Liu et al. Transforming growth factor-beta 1 delivery from microporous scaffolds decreases inflammation post-implant and enhances function of transplanted islets. Biomaterials. 2016;80:11-9.
Lu et al., Pancreatic beta-cell-specific repression of insulin gene transcription by CCAAT enhancer-binding protein beta—Inhibitory interactions with basic helix-loop-helix transcription factor E47. Journal of Biological Chemistry. 1997;272:28349-59.
Meirow et al., Ovarian tissue cryopreservation and transplantation: a realistic, effective technology for fertility preservation, Methods Mol. Biol., 1154:455-73 (2014).
Miller et al., Significance of Circulating Tumor Cells Detected by the CellSearch System in Patients with Metastatic Breast Colorectal and Prostate Cancer. J Oncol, 2010. 2010: p. 617421.
Moberg, The role of the innate immunity in islet transplantation. Upsala journal of medical sciences. 2005;110:17-55.
Nagaraj et al., Tumor escape mechanism governed by myeloid-derived suppressor cells. Cancer research, 2008. 68(8): p. 2561-2563.
Oktay et al., Embryo development after heterotopic transplantation of cryopreserved ovarian tissue, Lancet, 363(9412):837-40 (Mar. 2004).
Oktay et al., Endocrine function and oocyte retrieval after autologous transplantation of ovarian cortical strips to the forearm, JAMA, 286(12):1490-3 (Sep. 2001).
Ozmen et al., Inhibition of thrombin abrogates the instant blood-mediated inflammatory reaction triggered by isolated human islets: possible application of the thrombin inhibitor melagatran in clinical islet transplantation. Diabetes. 2002;51:1779-84.
Pagliuca et al. Generation of Functional Human Pancreatic beta Cells In Vitro. Cell. 2014;159:428-39.
Pagliuca et al., How to make a functional beta-cell. Development. 2013;140:2472-83.
Papavasiliou et al., Synthetic PEG Hydrogels as Extracellular Matrix Mimics for Tissue Engineering Applications, Biotechnol.—Mol. Stud. Nov. Appl. Improv. Qual. Hum. Life, 111-135 (2012).
Park et al. Exendin-4 uses Irs2 signaling to mediate pancreatic beta cell growth and function. The Journal of biological chemistry. 2006;281:1159-68.
Pauls et al., Function and regulation of zebrafish nkx2.2a during development of pancreatic islet and ducts. Developmental Biology. 2007;304:875-90.
Pearson et al., Controlled Delivery of Single or Multiple Antigens in Tolerogenic Nanoparticles Using Peptide-Polymer Bioconjugates, Mol. Ther., 25(7):1655-64 (Jul. 2017).
Qi et al. Implementation of a simplified method of islet isolation for allogeneic islet transplantation in cynomolgus monkeys. Pancreas. 2014;43:226-35.
Qin et al. Systematic Comparison of Constitutive Promoters and the Doxycycline-Inducible Promoter. Plos One. 2010;5.
Rahib et al., Projecting cancer incidence and deaths to 2030: the unexpected burden of thyroid, liver, and pancreas cancers in the United States, Cancer Res., 74(11):2913-21 (Jun. 2014).
Rezania et al. Enrichment of human embryonic stem cell-derived NKX6.1-expressing pancreatic progenitor cells accelerates the maturation of insulin-secreting cells in vivo. Stem Cells. pp. 2432-2442 (2013).
Rezania et al. Maturation of human embryonic stem cell-derived pancreatic progenitors into functional islets capable of treating pre-existing diabetes in mice. Diabetes. 2012;61:2016-29.
Rezania et al. Reversal of diabetes with insulin-producing cells derived in vitro from human pluripotent stem cells. Nature Biotechnology. 2014;32:1121-33.
Rhim et al., Detection of circulating pancreas epithelial cells in patients with pancreatic cystic lesions. Gastroenterology, 2014. 146(3): p. 647-51.
Rhim et al., EMT and dissemination precede pancreatic tumor formation. Cell, 2012. 148(1-2): p. 349-61.
Rios et al., Mold-casted non-degradable, islet macro-encapsulating hydrogel devices for restoration of normoglycemia in diabetic mice, Biotechnol. Bioeng., 113(11):2485-95 (Nov. 2016).
Rives et al., Layered PLG scaffolds for in vivo plasmid delivery. Biomaterials. 2009;30:394-401.
Rosendahl et al., The safety of transplanting cryopreserved ovarian tissue in cancer patients: a review of the literature, J. Assist. Reprod. Genet., 30(1):11-24 (Jan. 2013).
Salama et al., New advances in ovarian autotransplantation to restore fertility in cancer patients, Cancer Metastasis Rev., 34(4):807-22 (Dec. 2015).
Salvay et al. Extracellular matrix protein-coated scaffolds promote the reversal of diabetes after extrahepatic islet transplantation. Transplantation. 2008;85:1456-64.
Salvay et al., Gene delivery by surface immobilization of plasmid to tissue-engineering scaffolds. Gene Therapy. 2010;17:1134-41.
Schulz et al. A scalable system for production of functional pancreatic progenitors from human embryonic stem cells. PLoS One. 2012;7:e37004.

(56) References Cited

OTHER PUBLICATIONS

Seidlits et al., Hydrogels for lentiviral gene delivery. Expert Opinion on Drug Delivery. 10(4):499-509 (Apr. 2013).

Shea et al., Bioengineering the ovarian follicle microenvironment, Annu. Rev. Biomed. Eng., 16:29-52 (Jul. 2014).

Shepard et al., Hydrogel macroporosity and the prolongation of transgene expression and the enhancement of angiogenesis. Biomaterials. 2012;33:7412-21.

Shikanov et al., Fibrin encapsulation and vascular endothelial growth factor delivery promotes ovarian graft survival in mice, Tissue Eng. Part A, 17(23-24):3095-104 (Dec. 2011).

Shikanov et al., Hydrogel network design using multifunctional macromers to coordinate tissue maturation in ovarian follicle culture, Biomaterials, 32(10):2524-31 (Apr. 2011).

Siletz et al. Dynamic Transcription Factor Networks in Epithelial-Mesenchymal Transition in Breast Cancer Models. Plos One, 8(4):e57180, 2013.

Smith et al., Fibrin-mediated delivery of an ovarian follicle pool in a mouse model of infertility, Tissue Eng. Part A, 20(21-22):3021-30 (Nov. 2014).

Sneddon et al., Self-renewal of embryonic-stem-cell-derived progenitors by organ-matched mesenchyme. Nature. 2012:491:765.

Soares et al., Evaluation of a human ovarian follicle isolation technique to obtain disease-free follicle suspensions before safely grafting to cancer patients, Fertil. Steril., 104(3):672-80 e2 (Sep. 2015).

Stacer et al. NanoLuc Reporter for Dual Luciferase Imaging in Living Animals. Molecular Imaging. 12(7):1-13 (Oct. 2013).

Stoffel et al., Localization of human homeodomain transcription factor insulin promoter factor 1 (IPF1) to chromosome band 13q12. 1. Genomics. 1995;28:125-6.

Telfer et al., Ovarian follicle culture: advances and challenges for human and nonhuman primates, Fertil. Steril., 99(6):1523-33 (May 2013).

Thomas et al., Sponge-mediated lentivirus delivery to acute and chronic spinal cord injuries. Journal of Controlled Release. 2015;204:1-10.

Tuinstra et al., Multifunctional, multichannel bridges that deliver neurotrophin encoding lentivirus for regeneration following spinal cord injury, Biomaterials, 33(5):1618-26 (Feb. 2012).

Vaithilingam et al. Beneficial effects of coating alginate microcapsules with macromolecular heparin conjugates—in vitro and in vivo study. Tissue Eng Part A. 2014;20:324-34.

Valetti et al., Peptide conjugation: before or after nanoparticle formation?, Bioconjug. Chem., 25(11):1971-83 (Nov. 2014).

Vanacker et al., First transplantation of isolated murine follicles in alginate, Regen. Med., 9(5):609-19 (2014).

Villasenor et al., Crosstalk between the developing pancreas and its blood vessels: an evolving dialog. Semin Cell Dev Biol. 2012;23:685-92.

Wallace et al., Ovarian failure following abdominal irradiation in childhood: the radiosensitivity of the human oocyte, Br. J. Radiol., 62(743):995-8 (Nov. 1989).

Weiss et al. Dynamic transcription factor activity and networks during ErbB2 breast oncogenesis and targeted therapy. Integrative Biology. 2014;6:1170-82.

Weizman et al., The effect of endothelial cells on hESC-derived pancreatic progenitors in a 3D environment. Biomaterials Science. 2014;2:1706-14.

Wo et al., Impact of radiotherapy on fertility, pregnancy, and neonatal outcomes in female cancer patients, Int. J. Radiat. Oncol. Biol. Phys., 73(5):1304-12 (Apr. 2009).

Xiao et al., In vitro follicle growth supports human oocyte meiotic maturation, Sci. Rep., 5:17323 (Nov. 2015).

Xiao et al., Size-specific follicle selection improves mouse oocyte reproductive outcomes, Reproduction, 150(3):183-92 (Sep. 2015).

Xu et al., Secondary follicle growth and oocyte maturation by culture in alginate hydrogel following cryopreservation of the ovary or individual follicles, Biotechnol. Bioeng., 103(2):378-86 (Jun. 2009).

Xu et al., Tissue-engineered follicles produce live, fertile offspring, Tissue Eng., 12(10):2739-46 (Oct. 2006).

Yamamoto et al. A Novel Function of Onecut1 Protein as a Negative Regulator of MafA Gene Expression. Journal of Biological Chemistry. 2013;288:21648-58.

Yap et al. Collagen IV-modified scaffolds improve islet survival and function and reduce time to euglycemia. Tissue Eng Part A. 2013;19:2361-72.

Zhao et al. The islet beta cell-enriched MafA activator is a key regulator of insulin gene transcription. Journal of Biological Chemistry. 2005;280:11887-94.

\* cited by examiner

FUNCTIONALIZATION OF POLYMER SCAFFOLDS

CROSS-REFERENCE TO RELATED APPLICATION

The benefit under 35 U.S.C. § 119(e) of U.S. Provisional Patent Application No. 62/468,833 filed Mar. 8, 2017, is hereby claimed and the entire disclosure is incorporated herein by reference.

STATEMENT OF GOVERNMENT SUPPORT

This invention was made with government support under grant R01EB09910 awarded by the National Institutes of Health. The Government has certain rights in the invention.

FIELD OF THE DISCLOSURE

The disclosure relates generally to methods of preparing a functionalized polymer scaffold with control over the amount of functionalization of the polymer scaffold.

BACKGROUND

Delivery of proteins to cellular environments may be used to elicit desired responses from the cells. Attachment of proteins to polymer scaffolds represents a major advantage over other approaches, such as encapsulation, to provide cues to elicit desired responses from cells in the scaffold microenvironment. Current methods to functionalize polymer scaffolds involve modifying the polymer scaffold post scaffold preparation with proteins, peptides, or other small molecules. However, such post scaffold preparation modification methods are typically inefficient and inconsistent between batches. In particular, due to the porous nature of the polymer scaffolds it is difficult to provide a homogeneous coating of proteins, peptides, or other small molecules. Thus, a need exists for polymer scaffolds that can address these difficulties.

SUMMARY

One aspect of the disclosure provides a method of preparing a polymer scaffold including admixing a biotinylated reagent and a polymer to form a biotinylated polymer, subjecting the biotinylated polymer to conditions sufficient to form the polymer scaffold and optionally admixing the polymer scaffold with a streptavidin-modified biomolecule to form a biomolecule-modified polymer scaffold.

Another aspect of the disclosure provides a method of preparing a polymer scaffold including admixing a first click chemistry reagent and a poly(lactic co-glycolic acid) (PLGA) polymer to form a modified PLGA polymer, subjecting the modified PLGA polymer to conditions sufficient to form the polymer scaffold, and optionally admixing the polymer scaffold with a biomolecule modified to include a second click chemistry reagent that selectively reacts with the first click chemistry reagent, to form a biomolecule-modified polymer scaffold.

Another aspect of the disclosure provides a polymer scaffold including a plurality of microparticles of a polymer modified with a reactive handle, wherein the reactive handle is distributed homogeneously throughout the polymer scaffold, the reactive handle capable of reacting with a biomolecule to form a covalent or non-covalent bond between the biomolecule and the polymer scaffold.

Another aspect of the disclosure provides a polymeric structure comprising a plurality of polymer scaffolds, wherein the polymeric structure has a layered structure of the plurality of polymer scaffolds.

Further aspects and advantages will be apparent to those of ordinary skill in the art from a review of the following detailed description. While the compositions and methods are susceptible of embodiments in various forms, the description hereafter includes specific embodiments with the understanding that the disclosure is illustrative, and is not intended to limit the invention to the specific embodiments described herein.

DETAILED DESCRIPTION

Figure 1:
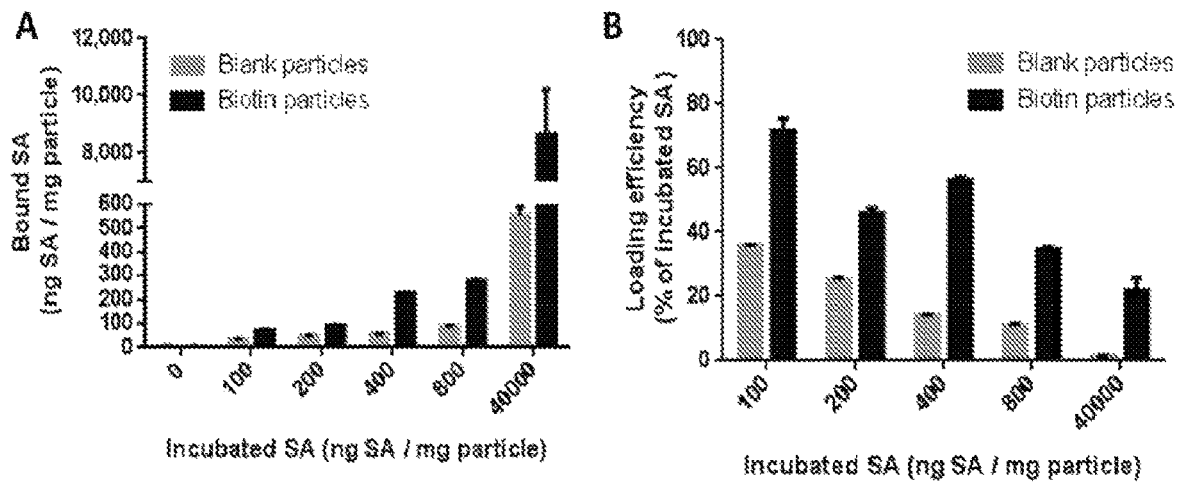
FIG. 1 shows (A) Streptavidin loading on biotin-PLGA particles and unmodified PLGA particles and (B) the loading efficiency of streptavidin to the PLGA particles.

Provided herein are functionalized polymer scaffolds, and methods of making and using functionalized polymer scaffolds. In general, methods of the disclosure utilize chemical functionalization of polymers with a reagent prior to scaffold preparation or formation, enabling control over the amounts of functionalization of the polymer scaffold. The methods disclosed herein provide one or more advantages, for example, providing a consistent method for preparing a polymer scaffold having a reactive handle or reagent conjugated thereto, providing control over molecular functionalization of the scaffolds, and providing scaffolds with localized molecules. Further, the disclosed methods allow for attaching a broad range of protein, peptides, or small molecules to the surface of the scaffold through the reactive handle or reagent, allowing for use in a wide range of applications. Thus, the methods herein can provide functionalized polymer scaffolds having one or more advantages such as a providing a known quantity of a reactive handle homogeneously throughout the scaffold and/or providing a layered polymer structure having functional groups purposely distributed spatially throughout the polymer structure. Non-limiting examples of applications include presenting immunoregulatory molecules to protect transplanted tissue, presenting growth factors to stimulate growth, differentiation, or proliferation, and presenting cell binding domains to provide physical cues and adhesion.

The scaffold can comprise a plurality of microparticles comprising a polymer modified with a reactive handle. The reactive handle can advantageously be distributed homogeneously throughout the polymer scaffold and is capable of reacting with a biomolecule to form a covalent or non-covalent bond between the biomolecule and the polymer scaffold.

As used herein the term "microparticle" refers to a particle of polymer matrix having a size in a range of about 0.1 and 100 micron.

Some or each of the plurality of microparticles can comprise the reactive handle. The amount of reactive handle provided on each of the plurality of microparticles, or in total in the polymer scaffold is not particularly limited. For example, the reactive handle can be provided on each of the plurality of microparticles in an amount in a range of 0.01 to 99 wt. %, 3-75 wt. %, 5-50 wt. %, 1-25 wt. %, or 2-10 wt. %, based on the total weight of the polymer scaffold. The amount of reactive handle provided on a microparticle can also be characterized by the weight percent of the reactive handle, based on the total weight of the microparticles. For example, the reactive handle can be provided on each of the plurality of microparticles in an amount in a range of 0.01-99 wt. %, 3-75 wt. %, 5-50 wt. %, 1-25 wt. %, or 2-10 wt. %, based upon the total weight of the microparticle.

In some cases, the amount of the reactive handle provided can be characterized as an effective amount to bring about a desired result. For example, the amount of reactive handle may be provided in an amount sufficient to bind a desired amount of biomolecule. More specifically, the amount of biomolecule bound to the polymer scaffold can be an amount effective to exert bioactivity on the cell type of interest, such as, inducing apoptosis in immune cells, inducing anti-inflammatory responses in immune cells, or creating an antigen-specific immune response. In some cases, the microparticles can include a predetermined amount of reactive handle. The predetermined amount of reactive handle can be any suitable amount, for example, the amounts provided herein. Advantageously, the microparticles can be designed to be loaded with a specifically selected amount of reactive handle to enable incorporation of precise amounts of bioactive molecules.

The polymer scaffold disclosed herein can be modified at the reactive handle with any entity of interest. In some cases, the entity is a biomolecule. The entity can be introduced to a polymer scaffold at a complementary functional group or feature to the reactive handle on the entity, e.g., via a covalent bond with on the reactive handle on the polymer, or through a non-covalent interaction, such as an ionic interaction or guest-host interaction, with the reactive handle and a complementary functional group or feature. As used herein, "complementary" indicates that the entity comprises a functional group or a feature that forms a covalent bond or non-covalent interaction with the reactive handle on the polymer scaffold. The reactive handle and the complementary functional group on the entity may together be referred to as a reactive pair. Reactive pairs are well known to one of ordinary skill in the art. Reactive pairs may include, but are not limited to, biotin and streptavidin, click chemistry reactive pairs, and other orthogonal reactive pairs. In some cases, the reagent or reactive handle comprises biotin or a click chemistry reagent. Click chemistry reactive pairs include a first click chemistry reagent (e.g., an azide) and a second, complementary click chemistry reagent (e.g., an alkyne). The click chemistry reagent can include a functional group selected from the group consisting of an azide, an alkyne, an amine, a carboxylic acid, a maleimide, a sulfhydryl, a vinyl sulfone, an acrylate, and combinations of the foregoing. It will be appreciated that either entity of the reactive pair can be incorporated into the polymer prior to scaffold formation (the "reagent" or "reactive handle"), while the other entity of the reactive pair ("the second reagent") can be incorporated into the molecule to be functionalized onto the polymer scaffold (e.g., a biomolecule). Additional suitable reactive pairs are well known in the art and include, but are not limited to, reactive pairs that couple amines to carboxylic acids, maleimides to sulfhydryls, vinyl sulfones to sulfhydryls, and acrylates to sulfhydryls.

The reagent or reactive handle is capable of reacting with a biomolecule to form a covalent or non-covalent bond between the biomolecule and the polymer scaffold. The reagent can be the specific protein, peptide, or small molecule that selectively reacts with the second reagent. The reagent or reactive handle of the polymer scaffold can further include a functional group to promote reaction or interaction with a reactive group of the polymer. For example, the reagent may comprise a biotinylated reagent, for example, a biotinylated poly(ethylene glycol) amine. The biotin moiety is the reactive functional group to associate with a streptavidin-modified biomolecule, for example. The amine moiety is the functional group used to interact with the polymer—to form a covalent bond with the polymer prior to scaffold formation. The poly(ethylene glycol) (PEG) moiety plays the role of a linker or spacer to separate the two features of the reagent. Suitable biotinylated poly(ethylene glycol) amines may include biotinylated poly(ethylene glycol) amines having repeating ethylene glycol (EG) monomers, oligomer chain, or low molecular weight chain, for example at least an EG monomer, at least a PEG dimer (i.e. PEG 2), at least a PEG trimer (i.e., PEG 3), at least PEG 10, and up to about PEG 100, up to about PEG 80, up to about PEG 50, up to about PEG 40, or up to about PEG 30. In some cases, the PEG is PEG 4 to PEG 50, PEG 4 to PEG 40, or PEG 4 to PEG 25.

The polymer which forms the scaffold can be any polymer that includes a functional group that can be modified to include a reagent or reactive handle. Suitable polymers may include functional groups such as carboxylic acids, alcohols, aldehydes, amines, amides, esters, and combinations thereof. Suitable polymers include, but are not limited to, poly(lactic co-glycolic acid), poly(lactic acid), poly(glycolic acid), poly(ethylene glycol), polycaprolactone, alginate, collagen, poly(amino acids), and combinations thereof. The polymers can be activated prior to reacting the polymers with the reagent, to introduce a reactive feature to the polymer that is then used to introduce the reagent of the reactive pair. Suitable activators are well known in the art and include, for example, a carbodiimide and one of N-hydroxysuccinimide (NHS), sulfo-NHS, hydroxybenzotriazole (HOBt), 1-hydroxy-7-azabenzotriazole (HOAt), pentafluorophenol, and combinations thereof.

In some cases, when the polymer includes poly(lactic-co-glycolic acid), the reagent comprises a first click chemistry reagent. In various cases, when the reagent comprises biotin, the polymer is selected from the group consisting of poly(lactic-co-glycolic acid), poly(ethylene glycol), polycaprolactone, alginate, and a combination thereof. As demonstrated in the Examples, a poly(lactic-co-glycolic acid) polymer can be modified to include a reagent through the carboxylic acid functionality of the polymer. It is understood that any polymer comprising a carboxylic acid functional group could be modified in the same way as poly(lactic-co-glycolic acid).

The polymers modified with a reagent or reactive handle can be formed into microparticles which in turn can be formed into a polymer scaffold. In some cases, the microparticles comprise a second polymer and the second polymer is an unmodified polymer. The unmodified polymer is not particularly limited and can be the same base polymer as the polymer having a reactive handle, or can be a different base polymer than the polymer having a reactive handle. In some embodiments, the unmodified polymer is selected from the group consisting poly(lactic co-glycolic acid), poly(lactic acid), poly(glycolic acid), poly(ethylene glycol), polycaprolactone, alginate, collagen, poly(amino acids), and a combination thereof. The polymer modified with a reactive handle and the unmodified polymer can be provided in a weight ratio of about 100:1 to about 1:100, based on the total weight of the polymers, for example, about 50:1 to about 1:50, about 25:1 to about 1:25, about 1:10 to about 10:1, about 1:5 to about 5:1, about 1:3 to about 3:1, about 1:1 to about 3:1, about 1:1 to about 4:1, or about 1:1 to about 5:1.

The polymers modified with a reagent can be formed into a polymer scaffold and, optionally, further reacted with an entity having a second reagent having selectivity for the reagent. In some cases, the entity having a second reagent having selectivity for the reagent is a biomolecule to provide a biomolecule-modified polymer scaffold. As used herein, the term "biomolecule" refers to an antibody, antigen, protein, enzyme, peptide, oligonucleotide, polynucleotide, oligosaccharide, polysaccharide, or small molecule (e.g., therapeutic agent or fluorophore) thereof. In some cases, the biomolecule comprises FasL. In some cases, the biomolecule comprises FasL, IL-2, TGF-beta, IL-10 or a cell lysate. The biomolecule can further comprise biotin, straptavidin, or a click chemistry reagent as a second reagent.

In some cases, the polymer scaffold includes a biomolecule that includes a click chemistry reagent and a reactive handle that includes a complementary click chemistry reagent. In some cases, the polymer scaffold includes a biomolecule that includes biotin and a reactive handle that includes streptavidin, or vice versa.

Figure 8:
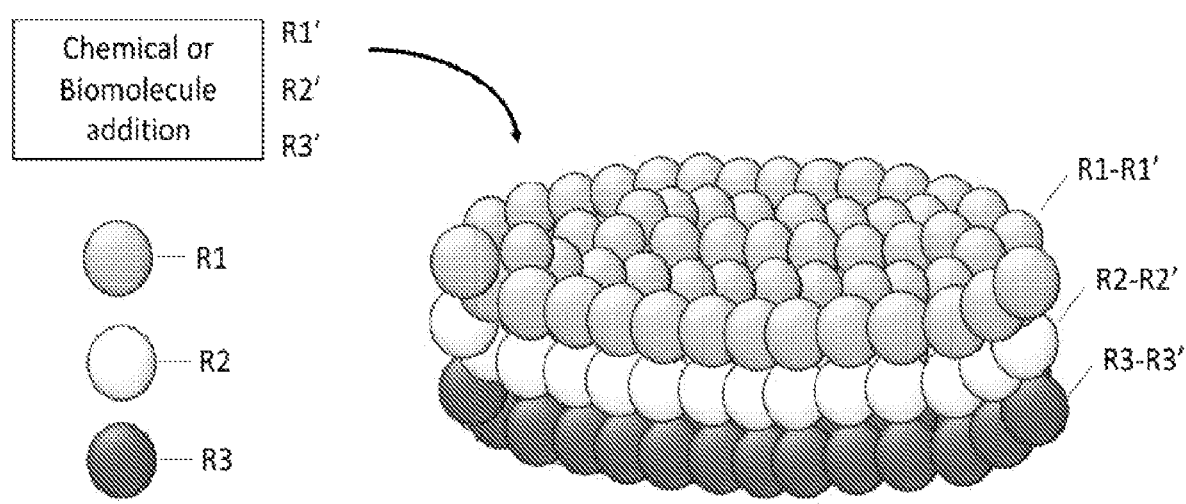
FIG. 8 depicts a polymeric structure having a plurality of scaffold layers, wherein each scaffold layer includes a functional handle (R1, R2, or R3) which can further include chemical or biomolecules having reactive groups complementary to the functional handle.

The plurality of polymer microparticles can be fused together to form the polymer scaffold. A plurality of polymer scaffolds can be layered to provide a polymeric structure. Each of the polymer scaffolds that make up the polymeric structure can include one or more reactive handles. The polymeric structures can be designed to have one or more advantages including, but not limited to, reactive handles and, optionally, biomolecules purposely distributed throughout the scaffold. As depicted in FIG. 8, polymers having a reactive handle can be blended at controlled ratios with unmodified polymers and subsequently formed into polymer microparticles to precisely incorporate known amounts of reactive handles onto the surface of individual particles (R). Particles can be prepared to incorporate blends of reactive handless or single types of reactive handless that have various properties including labile or stimuli-responsive bonds or non-covalent interactions. The scaffolds can be layered to distribute the various functional groups spatially throughout the polymeric structure. A mixture of chemical or biomolecules with complementary reagents (R') to those on the particles can be incubated with the polymer structure to yield a structure with multiple layers that simultaneously deliver critical chemical or biomolecular cues (R—R'). When necessary, the addition of the chemical or biomolecules can be performed sequentially.

The disclosure provides methods of preparing a polymer scaffold comprising (a) admixing a biotinylated reagent and a polymer to form a biotinylated polymer, (b) subjecting the biotinylated polymer to conditions sufficient to form the polymer scaffold and optionally (c) admixing the polymer scaffold with a streptavidin-modified biomolecule to form a biomolecule-modified polymer scaffold. In some cases, the biotinylated reagent comprises a biotinylated poly(ethylene glycol) amine. In various cases, the polymer is selected from the group consisting of poly(lactic-co-glycolic acid), poly (ethylene glycol), polycaprolactone, alginate, and a combination thereof. The polymer can be activated to react with the biotinylated reagent, for example, an activated poly (lactic-co-glycolic) acid.

Admixing the biotinylated reagent and the polymer to form a biotinylated polymer can be carried out under any conditions suitable to form the biotinylated polymer. Suitable conditions are well known to one of ordinary skill in the art. For example, the polymer can be dissolved in a solvent, optionally activated, and admixed with a biotinylated reagent, at ambient conditions. The ratio of reagent to polymer can be selected to provide the desired amount of functionalization of the polymer. Suitably, the reagent can be added in an amount to provide a reagent to polymer molar ratio of about 1:1 to about 1000:1, for example, about 1:1 to about 750:1, about 1:1 to about 500:1, about 1:1 to about 250:1, about 1:1 to about 100:1, about 1:1 to about 50:1, or about 1:1 to about 25:1.

Polymer scaffolds can be formed directly from the biotinylated polymers and/or from microparticles prepared from the biotinylated polymers. Thus, conditions sufficient to form the polymer scaffold can include forming microparticles or microspheres from the polymer prior to forming the polymer scaffold. In some cases, the conditions sufficient to form the polymer scaffold comprise contacting the biotinylated polymer with a second polymer. The second polymer can be a non-biotinylated polymer, and can be the same or different from the polymer that is biotinylated.

When the conditions sufficient to form the polymer scaffold include forming microparticles or microspheres, forming the microparticles or microspheres can include contacting the biotinylated polymer with a second, non-biotinylated polymer. Microspheres are a specific type of microparticles that are formed from a combination of biotinylated polymer with a non-biotinylated polymer.

When the conditions sufficient to form the polymer scaffold include contacting the biotinylated polymer with a second polymer, the biotinylated polymer and the second polymer can be provided in a weight ratio of about 100:1 to about 1:100, based on the total weight of the polymers, for example, about 50:1 to about 1:50, about 25:1 to about 1:25, about 1:10 to about 10:1, about 1:5 to about 5:1, about 1:3 to about 3:1, about 1:1 to about 3:1, about 1:1 to about 4:1, or about 1:1 to about 5:1.

Conditions sufficient to form the polymer scaffold can further include fusing together a plurality of polymers or a plurality of microparticles or microspheres. Methods of fusing together a plurality of polymers or a plurality of microparticles or microspheres are known in the art, for example, by solvent evaporation or by subcritical $CO_2$ sintering. In particular, the scaffolds can be formed by a solvent casting approach wherein the polymer is dissolved in a solvent and mixed with a salt, with subsequent removal of the solvent, and leaching of the salt to form a porous scaffold. Alternatively, scaffolds can be formed by mixing the polymers with a salt, pressing the mixture into a KBr die, and foaming in $CO_2$ at 750 psi, followed by removal of the salt to form a porous scaffold. The salt used to prepare the polymer scaffold may be any water-soluble salt, including but not limited to chloride, bromide, and iodide alkali metal salts. Advantageously, because the biotinylated polymer is dispersed within the polymer scaffold, the polymer scaffold includes a homogeneous distribution of biotin functionalization.

In some cases, the polymer scaffold is admixed with a streptavidin-modified biomolecule to form a biomolecule-modified polymer scaffold. In various cases, the biomolecule is an antibody, antigen, protein, enzyme, peptide, oligonucleotide, polynucleotide, oligosaccharide, polysaccharide, or small molecule (e.g., therapeutic agent or fluorophore). In some cases, the biomolecule comprises FasL. In some cases, the biomolecule comprises FasL, IL-2, TGF-beta, IL-10, or a cell lysate.

The amount of biomolecule provided is not particularly limiting. In general, the amount of biomolecule provided can be any amount sufficient to provide a desired effect. For example, the biomolecule can be provided in an amount sufficient to induce apoptosis in immune cells. The polymer scaffold and streptavidin-modified biomolecule can be admixed at a concentration in a range of about 2 to about 200,000 ng streptavidin-modified biomolecule per mg scaffold, for example about 50 ng to about 150,000 ng, about 100 ng to about 140,000 ng, about 200 ng to about 130,000 ng, about 400 ng to about 120,000 ng, about 800 ng to about 110,000 ng, about 1,000 ng to about 100,00 ng, or about 2 ng to about 1,000 ng, for example, about 100 ng, about 500 ng, about 1,000 ng, about 5,000 ng, about 10,000 ng, about 20,000 ng, about 40,000 ng, or about 60,000 ng streptavidin-modified biomolecule per mg scaffold.

In some cases, the polymer comprises poly(lactic-co-glycolic acid), the biotinylated reagent comprises biotinylated PEG 2 amine, and the streptavidin modified biomolecule comprises FasL.

The disclosure further provides methods of preparing a polymer scaffold comprising (a) admixing a first click chemistry reagent and a poly(lactic co-glycolic acid) (PLGA) polymer to form a modified PLGA polymer, (b) subjecting the modified PLGA polymer to conditions sufficient to form the polymer scaffold, and optionally (c) admixing the polymer scaffold with a biomolecule modified to include a second click chemistry reagent that selectively reacts with the first click chemistry reagent to form a biomolecule-modified polymer scaffold.

In some cases, the polymer can be activated to react with the first click chemistry reagent. In various cases, the first click chemistry reagent comprises an alkyne and the second click chemistry reagent comprises an azide. Alternatively, the first click chemistry reagent comprises an azide and the second click chemistry reagent comprises an alkyne.

Admixing the first click chemistry reagent and the PLGA polymer to form a modified PLGA polymer can be carried out under any conditions suitable to form the modified PLGA polymer. Suitable conditions are well known to one of ordinary skill in the art. For example, the polymer may be dissolved in a solvent, optionally activated, and admixed with an excess of a first click chemistry reagent, at ambient conditions. The ratio of reagent to polymer can be selected to provide the desired amount of functionalization of the polymer. Suitably, the reagent can be added in an amount to provide a reagent to polymer molar ratio of about 1:1 to about 1000:1, for example, about 1:1 to about 750:1, about 1:1 to about 500:1, about 1:1 to about 250:1, about 1:1 to about 100:1, about 1:1 to about 50:1, or about 1:1 to about 25:1.

Polymer scaffolds can be formed directly from the modified PLGA polymers and/or from microparticles prepared from the modified PLGA polymers. Thus, conditions sufficient to form the polymer scaffold can include forming microparticles or microspheres from the polymer prior to forming the polymer scaffold. In some cases, the conditions sufficient to form the polymer scaffold comprise contacting the modified PLGA polymer with a second polymer. The second polymer can be a non-modified polymer, and can be a non-modified PLGA polymer or a different polymer, for example, selected from the group consisting of poly(ethylene glycol), polycaprolactone, alginate, and a combination thereof.

When the conditions sufficient to form the polymer scaffold include forming microparticles or microspheres, forming the microparticles or microspheres can comprise contacting the modified PLGA polymer with a second, non-modified polymer. Microspheres can be formed when the microparticles are formed from a combination of modified PLGA polymer with a non-modified polymer.

When the conditions sufficient to form the polymer scaffold include contacting the modified PLGA polymer with a second polymer, the modified PLGA polymer and the second polymer can be provided in a weight ratio of about 100:1 to about 1:100, based on the total weight of the polymers, for example, about 50:1 to about 1:50, about 25:1 to about 1:25, about 1:10 to about 10:1, about 1:5 to about 5:1, about 1:3 to about 3:1, about 1:1 to about 3:1, about 1:1 to about 4:1, or about 1:1 to about 5:1.

Conditions sufficient to form the polymer scaffold further include fusing together a plurality of polymers or a plurality of microparticles or microspheres. Methods of fusing together a plurality of polymers or a plurality of microparticles or micro spheres are known in the art, for example, by solvent evaporation or by subcritical $CO_2$ sintering. In particular, the scaffolds can be formed by a solvent casting approach wherein the polymer is dissolved in a solvent and mixed with a salt, with subsequent removal of the solvent, and leaching of the salt to form a porous scaffold. Suitable solvents are any solvent that dissolve the polymer and can include, but are not limited to dichloromethane, chloroform, and acetone.

Alternatively, scaffolds can be formed by mixing the polymers with a salt, pressing the mixture into a KBr die, and foaming in $CO_2$ at 750 psi, followed by removal of the salt to form a porous scaffold. The salt used to prepare the polymer scaffold can be any water-soluble salt, including but not limited to chloride, bromide, and iodide alkali metal salts. The salt can be included in any amount to achieve the desired porosity. For example, the polymer to salt weight ratio can be in a range of about 1:5 to about 1:100, about 1:5 to about 1:80, about 1:10 to about 1:60, about 1:15 to about 1:50, about 1:20 to about 1:40, or about 1:25 to about 1:35. Advantageously, because the modified PLGA polymer is dispersed throughout the polymer scaffold, the polymer scaffold includes a homogeneous distribution of the first click chemistry reagent.

The porous polymer scaffold can be disinfected, for example, by washing in a 70% ethanol solution. Additionally, the polymer scaffold can be sterilized, for example, by gamma irradiation or ethylene oxide sterilization.

In some cases, the polymer scaffold can be admixed with a biomolecule modified to include a second click chemistry reagent that selectively reacts with the first click chemistry reagent to form a biomolecule-modified polymer scaffold. The biomolecule can be an antibody, antigen, protein, enzyme, peptide, oligonucleotide, polynucleotide, oligosaccharide, polysaccharide, or small molecule (e.g., therapeutic agent or fluorophore). In some cases, the biomolecule comprises FasL. In some cases, the biomolecule comprises IL-2 or a cell lysate.

The amount of biomolecule provided is not particularly limiting. In general, the amount of biomolecule provided can be any amount sufficient to provide a desired effect. For example, the biomolecule can be provided in an amount sufficient to induce apoptosis in immune cells. The polymer scaffold and biomolecule modified to include a second click chemistry reagent that selectively reacts with the first click chemistry reagent can be admixed at a concentration in a range of about 2 to about 200,000 ng second click chemistry reagent-modified biomolecule per mg scaffold, for example about 50 ng to about 150,000 ng, about 100 ng to about 140,000 ng, about 200 ng to about 130,000 ng, about 400 ng to about 120,000 ng, about 800 ng to about 110,000 ng, about 1,000 ng to about 100,00 ng, or about 2 ng to about 1,000 ng, for example, about 100 ng, about 500 ng, about 1,000 ng, about 5,000 ng, about 10,000 ng, about 20,000 ng, about 40,000 ng, or about 60,000 ng second click chemistry reagent-modified biomolecule per mg scaffold.

The above described aspects and embodiments can be better understood in light of the following examples, which are merely intended to be illustrative and are not meant to limit the scope in any way.

EXAMPLES

Example 1: Biotinylation of PLGA

Figure 7:
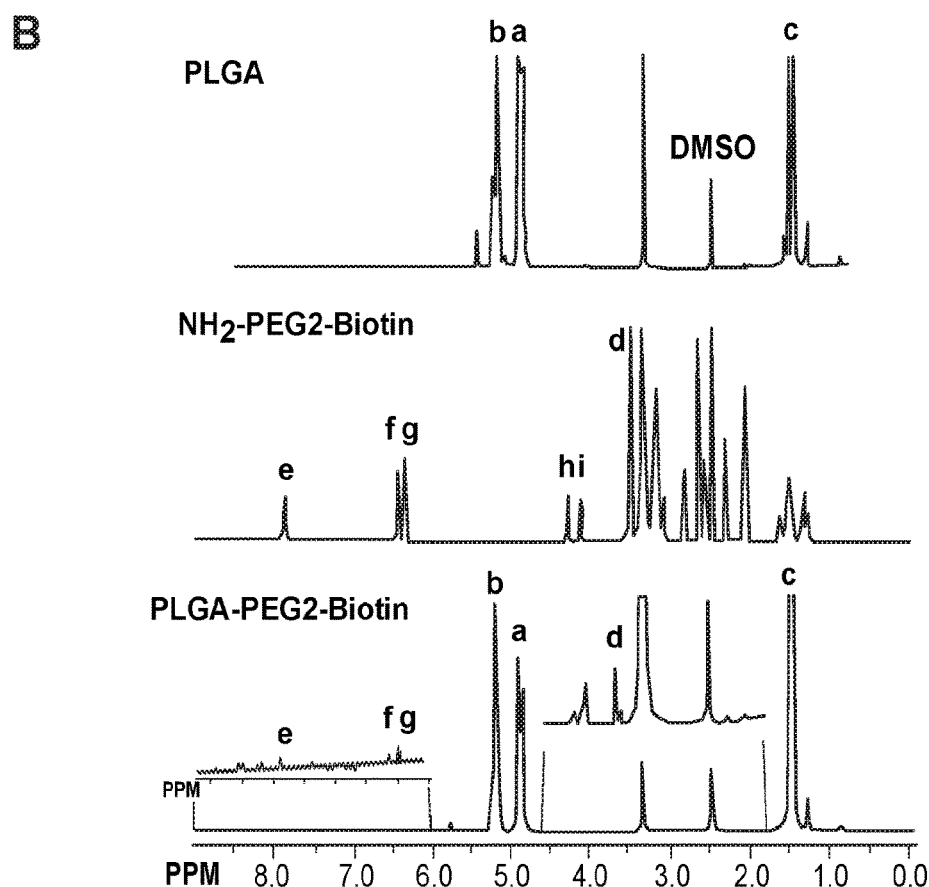
FIG. 7 shows (A) conjugation of $NH_2$-$PEG_2$-biotin to PLGA resulting in biotin-PLGA, (B) $^1$H-NMR in $(D_3C)_2SO$ of PLGA (top), biotin linker (middle), and biotin-PLGA (bottom), (C) size (860±40 nm) and charge (−15.8±4.98 mV) of biotin-PLGA particles measured using dynamic light scattering (DLS), and (D) scanning electron microscope (SEM) image of biotin-PLGA particles.
Figure 7:
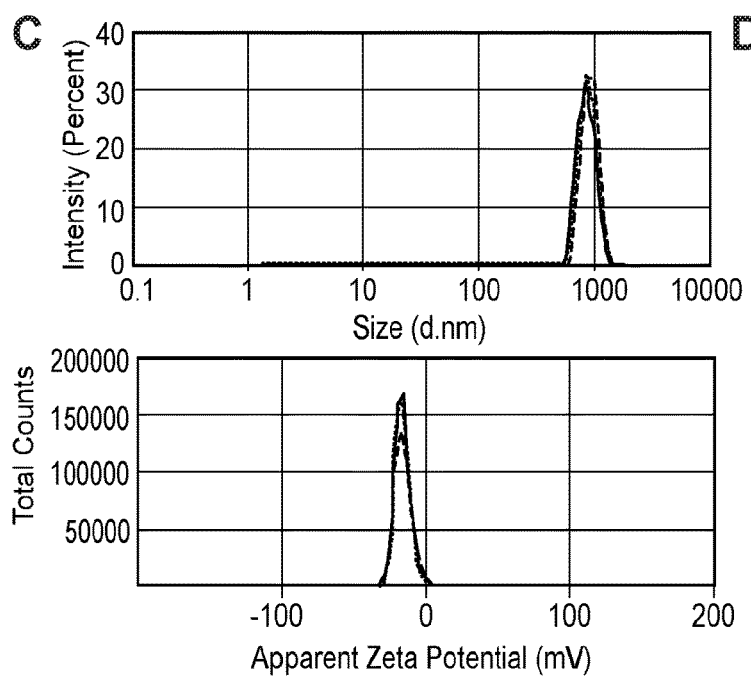
Figure 7:
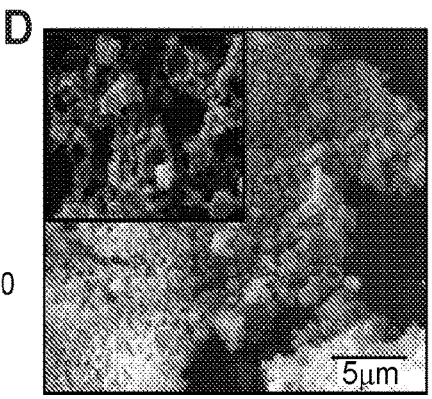

Poly(lactic-co-glycolic acid) (PLGA) (75:25 mole ratio of lactide to glycolide, 0.76 dL/g) was dissolved in dimethyl sulfoxide (DMSO) at a 1:15 weight ratio (PLGA:DMSO). The carboxylic acid of the PLGA was activated with 1-ethyl-3-(3-dimethylaminopropyl) carbodiimide hydrochloride (EDC) and N-hydroxysuccinimide (NHS). EDC and NHS were each dissolved in 1 mL of DMSO and added to the PLGA mixture for a final 5×molar excess to the PLGA. Biotin-PEG$_2$-NH$_2$ was dissolved in 1 mL DMSO and added to the activated PLGA mixture. The mixture was allowed to react overnight while mixing. Excess biotin was removed by extracting with 150 mL of saturated brine four times. The solution was dried with anhydrous sodium sulfate, then the volume was reduced by rotary evaporation. The biotinylated PLGA was precipitated in ice cold methanol and then stored in a vacuum oven overnight to remove residual methanol. Functionalization was confirmed with $^1$H NMR (($D_3C$)$_2$SO) as shown in FIG. 7. Thus Example 1 demonstrates preparation of a biotinylated polymer according to the disclosure.

Example 2: Biotin-PLGA Microparticle Formation

Figure 6:
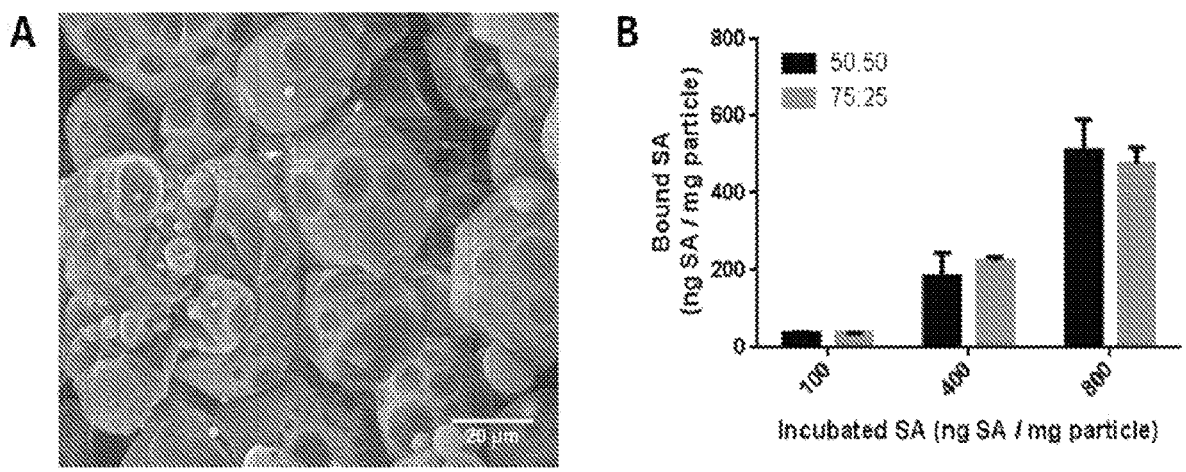
FIG. 6 shows (A) particles formed only with biotin-PLGA polymers and (B) loading on particles formed from biotin-PLGA and unmodified PLGA.

Biotin-PLGA prepared according to Example 1 was dissolved in dichloromethane (DCM) with non-modified PLGA at a ratio of 75:25 (biotin-PLGA:PLGA) for a final concentration of 6 wt % polymer in DCM. The solution was sonicated in a 1% poly(ethyl methacrylate) (PEMA) solution at 100% amplitude. The DCM was evaporated by stirring the emulsion overnight, followed by four washes to remove the PEMA. Particles were lyophilized for 48 hours and stored under vacuum. FIG. 7 shows the size (860±40 nm) and charge (−15.8±4.98 mV) of the biotinylated PLGA determined by dynamic light scattering. FIGS. 6 and 7 further show the scanning electron microscope image of biotin-PLGA particles.

Particles were similarly formed using biotin-PLGA:PLGA ratios of 50:50 and 100:0 (i.e., biotin-PLGA only). The spherical shape was confirmed with scanning electron microscopy (SEM). The microparticles formed using the combination of biotin-PLGA and non-modified PLGA consistently formed spherical particles. Thus, Example 2 demonstrates preparation of biotinylated polymer microparticles and microspheres according to the disclosure.

Example 3: Biotin-PLGA Polymer Scaffold Formed from Biotin-PLGA Microparticles

Porous scaffolds were formed by mixing biotin-PLGA microparticles prepared according to Example 2 with NaCl (250 μm<d<425 μm; wherein d is the average particle diameter) at a 1:30 ratio PLGA:NaCl. The mixture was pressed in a 5 mm KBr die using a Carver press, or equivalent, at 1500 psi. The resulting disk was loaded into a pressure vessel and foamed in $CO_2$ at about 750 psi for 8 to 24 hours, e.g., 16 hours to provide a salt/polymer construct. Porous scaffolds were prepared by leaching the salt from the construct by placing the construct in water for an hour followed by a second wash for 30 minutes. Scaffolds were disinfected by soaking in 70% ethanol and washed with water. Thus, Example 3 demonstrates preparation of functionalized polymer scaffolds according to the disclosure.

Example 4: Biotin-PLGA Polymer Scaffold Formed from Biotin-PLGA Polymers

Porous scaffolds were formed by mixing biotin-PLGA polymers prepared according to Example 1. NaCl (250 μm<d<435 μm) was loaded into a 5 mm KBr die. The biotin-PLGA polymers were dissolved in an organic solvent and poured over the salt such that the ratio of biotin-PLGA:NaCl was about 1:30. The solvent was allowed to evaporate, resulting in a salt/polymer construct. The construct was leached in water for an hour followed by a second wash for 30 minutes. The resulting porous scaffold was disinfected by soaking in 70% ethanol and washed in water. Thus, Example 4 demonstrates preparation of functionalized polymer scaffolds according to the disclosure.

Example 5: Conjugation of Reactive Pairs on Polymer Scaffold

Biotin-PLGA microparticles prepared according to Example 2 and porous scaffolds prepared according to Example 3 were further modified with streptavidin. In particular, biotin-PLGA microparticles were incubated with fluorescently-tagged streptavidin at a concentration of 1 mg particles/mL for 20 minutes. Unbound streptavidin was removed by rinsing the particles with phosphate buffer solution (PBS) twice. Particles were dissolved in DMSO and fluorescence was quantified on a plate reader, Synergy 2 (BioTek) or equivalent, using an excitation and emission of 578 and 605 nm, respectively.

To quantify the protein loading capacity of the biotinylated particles, fluorescently-tagged streptavidin was incubated at concentrations of 100, 200, 400 or 800 ng streptavidin per mg of particles for 15 minutes. The particles were then washed three times with PBS to remove non-binding protein, dissolved in DMSO, and fluorescence was measured. The corresponding loading concentrations were 75-280 ng streptavidin per mg of particles, and the loading efficiency (defined as the amount of protein bound divided by the amount incubated) decreased from 75% to 35% over this range as the particles became saturated with protein (FIG. 1). Saturation of the particles was achieved by incubating the particles in a 40,000 ng streptavidin per mg particles solution, which bound 8600 ng streptavidin per mg particles. To demonstrate that the protein binding is due to the biotin-streptavidin interaction and not passive adsorption of protein to the particle surface, unmodified PLGA microparticles were used as a control and demonstrated significantly lower binding and lower binding efficiency.

Similarly, biotin-PLGA scaffolds were incubated with fluorescent streptavidin by applying 10 µL of the streptavidin solution to both sides of the scaffold disc (a total of 20 µL) for 20 minutes. Unbound streptavidin was removed by washing the scaffold three times with PBS. Scaffolds were dissolved in DMSO and fluorescence was quantified.

Figure 3:
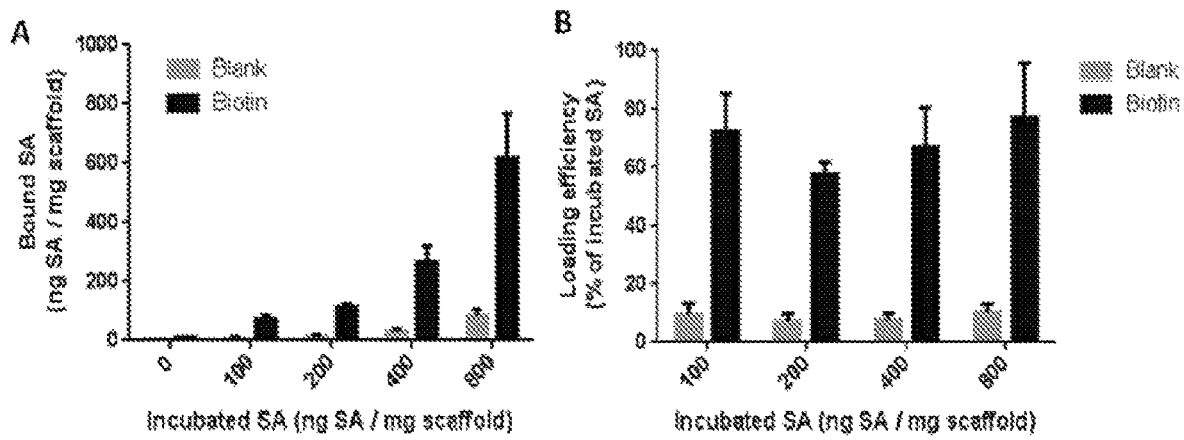
FIG. 3 shows (A) Streptavidin loading on biotin-PLGA scaffolds and unmodified PLGA scaffolds and (B) the loading efficiency of streptavidin to the PLGA scaffolds.

Protein binding to biotinylated scaffolds was quantified by incubating the scaffolds with 100, 200, 400, or 800 mg of fluorescently tagged streptavidin per mg of scaffold (one scaffold weights about 2.5 mg) for 15 minutes, washed to remove non-binding streptavidin, dissolved in DMSO, and quantified by fluorescence. The amount of bound streptavidin ranged from 70 to 620 ng streptavidin per mg of scaffold, similar to the microparticle loading at low concentrations, but over twice as much at higher concentrations (FIG. 3). Without intending to be bound by theory, it is believed that the increase in the amount of bound streptavidin for the scaffolds is due to the increased surface area of the porous scaffold as compared to the spherical microparticles. The loading efficiency of the scaffolds for all conditions tested was near 70%, with no decline in efficiency at higher protein concentrations, indicating that the scaffolds are capable of binding protein at considerably higher concentrations that what was tested. Unmodified scaffolds were used as a control and showed similar concentrations of non-specific binding to unmodified microparticles at higher protein concentrations. Thus, Example 5 demonstrates functionalization of a polymer microparticle or scaffold with a reactive pair according to the disclosure.

Example 6: FasL Loading on Biotin-PLGA Microparticles

Figure 2:
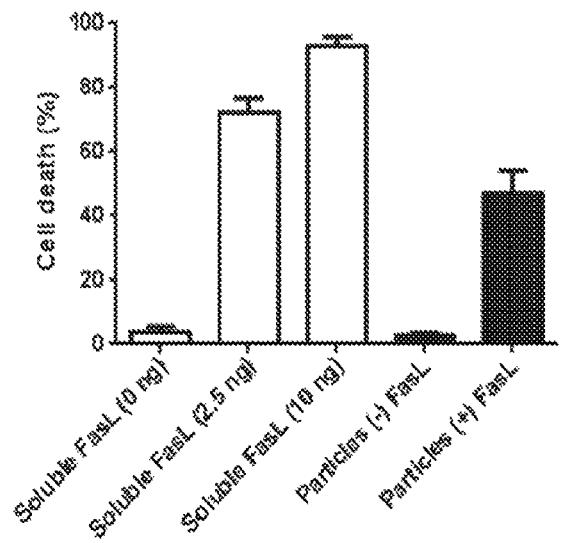
FIG. 2 shows inducement of A20 cell death by biotin-PLGA particle functionalized with SA-FasL relative to soluble FasL.

Biotin-PLGA particles having a mean particle diameter of 860±40 nm, as measured by DLS, were prepared according to Example 2. Utilizing the information from the binding curves prepared from Example 5, it was determined that one milligram of biotin-PLGA particles incubated with 400 ng streptavidin-FasL should bind sufficient amounts of protein to induce apoptosis. Particles were incubated with streptavidin-FasL, washed three times with PBS, and incubated with $1.5 \times 10^5$ A20 cells (mouse B lymphoma cells) for 18 hours. Following incubation, cell death was quantified via propidium iodide and flow cytometry. As a positive control, soluble FasL was included at concentrations known to induce apoptosis. While biotin particles not functionalized with FasL showed no difference in cell death, cells incubated with FASL-modified particles induced cell death in 50% of the population (FIG. 2). Thus, Example 6 demonstrates a biomolecule-modified microparticle prepared from biotinylated microparticles of the disclosure.

Example 7: FasL Loading on Biotin-PLGA Scaffolds

Figure 4:
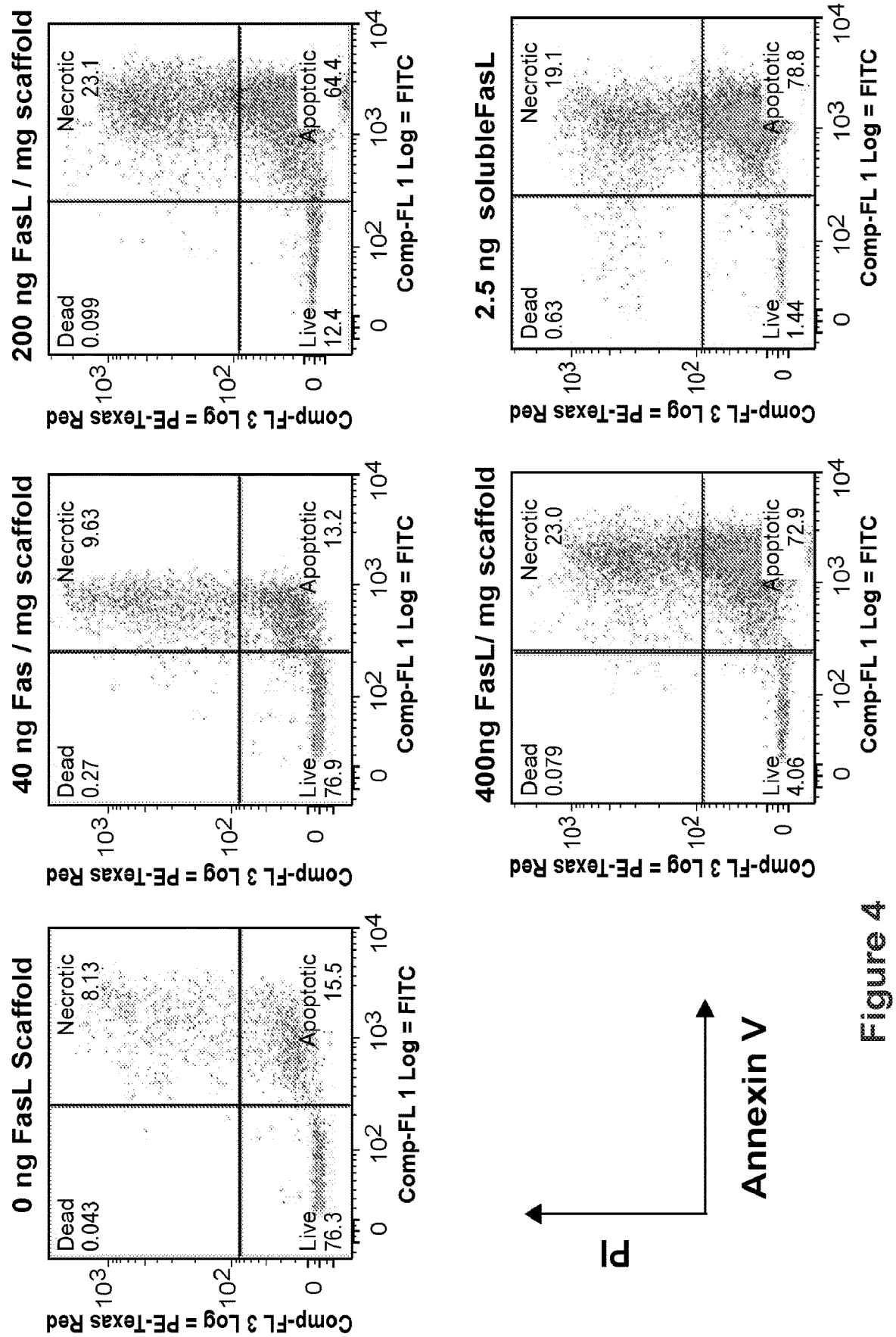
FIG. 4 shows inducement of A20 cell apoptosis by biotin-PLGA scaffolds functionalized with SA-FasL relative to soluble FasL.
Figure 5:
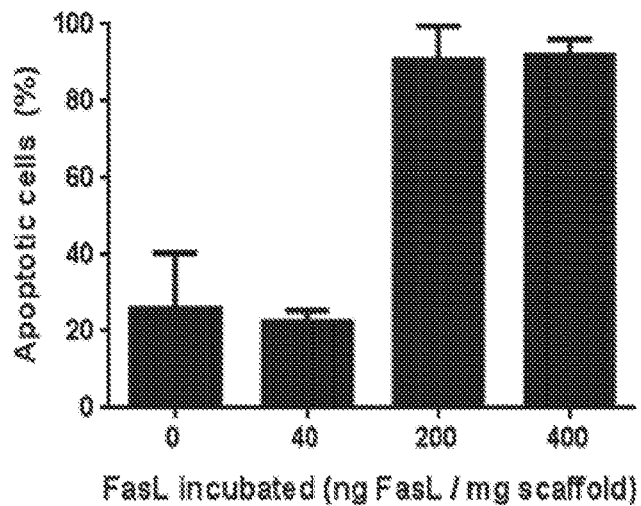
FIG. 5 shows biotin-PLGA scaffolds required a minimum loading of 200 ng FasL/mg scaffold to induce apoptosis in the majority of A20 cells.

Biotin-PLGA scaffolds were prepared according to Example 3. Particles were incubated with streptavidin-FasL to provide 400 ng FasL per mg of scaffold, washed three times with PBS, and incubated with $1.5 \times 10^5$ A20 cells (mouse B lymphoma cells) for 18 hours. Following incubation, an annexin V kit and flow cytometry was utilized to detect cells displaying phosphatidylserine (PS), a protein present on the surface of apoptotic cells. 400 ng FasL per mg of scaffold was sufficient to induce apoptosis in the majority of A20 cells (FIG. 4). Biotin-PLGA scaffolds required a minimum loading of 200 ng FasL/mg scaffold to induce apoptosis in the majority of A20 cells (FIG. 5). Thus, Example 7 demonstrates biomolecule-modified scaffolds according to the disclosure.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer, component, or step or groups of integers, components, or steps but not to the exclusion of any other integer, component, or step or groups of integers, components, or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

What is claimed:

1. A polymer scaffold comprising:
   a scaffold of a plurality of microparticles comprising a polymer modified to have a reactive handle, wherein the reactive handle is distributed homogeneously throughout the polymer scaffold, the reactive handle capable of reacting with a biomolecule to form a covalent or non-covalent bond between the biomolecule and the polymer scaffold, wherein the microparticles further comprise a second polymer and the second polymer is not modified with a reactive handle and the polymer modified to have a reactive handle and the second polymer are provided in a weight ratio of about 100:1 to 1:100; and
   wherein the reactive handle is provided in an amount sufficient to bind the biomolecule in an amount sufficient to exert a bioactivity, and
   wherein the microparticles are microspheres and the microspheres are arranged in a layer.

2. The polymer scaffold of claim 1, wherein each of the plurality of microparticles comprise a predetermined amount of reactive handle.

3. The polymer scaffold of claim 1, wherein the reactive handle comprises biotin or a click chemistry reagent.

4. The polymer scaffold of claim 3, wherein the click chemistry reagent comprises a functional group selected from the group consisting of an azide, an alkyne, an amine, a carboxylic acid, a maleimide, a sulfhydryl, a vinyl sulfone, and an acrylate.

5. The polymer scaffold of claim 1, wherein the polymer is selected from the group consisting of poly(lactic-co-glycolic acid), poly(ethylene glycol), poly(lactic acid), poly (glycolic acid), polycaprolactone, alginate, collagen, poly (amino acids), and a combination thereof.

6. The polymer scaffold of claim 1, wherein the unmodified polymer is selected from the group consisting of poly(lactic-co-glycolic acid), poly(lactic acid), poly(glycolic acid), poly(ethylene glycol), polycaprolactone, alginate, collagen, poly(amino acids), and a combination thereof.

7. The polymer scaffold of claim 1, further comprising the biomolecule.

8. The polymer scaffold of claim 7, wherein the biomolecule comprises an antibody, antigen, protein, enzyme, peptide, oligonucleotide, polynucleotide, oligosaccharide, polysaccharide, or small molecule.

9. The polymer scaffold of claim 7, wherein the biomolecule is modified to include biotin, streptavidin, or a click chemistry reagent which is capable of reacting with the reactive handle.

10. The polymer scaffold of claim 9, wherein the biomolecule is modified to include a click chemistry reagent, biotin, or streptavidin and the reactive handle comprises a complementary click chemistry reagent, streptavidin, or biotin.

11. A polymeric structure comprising a plurality of polymer scaffolds according to claim 1, wherein the polymeric structure has a layered structure of the plurality of polymer scaffolds.

12. The polymer scaffold of claim 1, wherein the polymer scaffold is porous and has a predefined porosity.

13. The polymer scaffold of claim 12, wherein the predefined porosity is in a range of about 50-99%.

14. The polymer scaffold of claim 1, wherein the polymer scaffold comprises pores having pore size in a range of about 250-435 µm.

15. The polymer scaffold of claim 1, wherein the polymer scaffold is capable of delivering the biomolecule to a cellular environment in a body.

16. The polymer scaffold of claim 1, wherein the microparticles have a particle size in a range of about 0.1-100 µm.

17. The polymer scaffold of claim 1, wherein the amount of the reactive handle is a predefined amount, and the amount of the biomolecule is a predetermined amount.

18. The polymer scaffold of claim 1, wherein the biomolecule comprises one or more of alginate, FasL and a cell lysate.

19. The polymer scaffold of claim 1, wherein the polymer comprises poly(lactic-co-glycolic acid).

20. The polymer scaffold of claim 1, wherein the reactive handle comprises biotinylated poly(ethylene glycol) (PEG) amine.

21. The polymer scaffold of claim 1, wherein the second polymer is the same type of polymer as the polymer modified to have the reactive handle, but the second polymer does not include the reactive handle.

22. The polymer scaffold of claim 1, wherein the polymer scaffold is sterilized or disinfected.

* * * * *